United States Patent [19]
Johansen et al.

[11] Patent Number: 5,549,659
[45] Date of Patent: Aug. 27, 1996

[54] COMMUNICATION INTERFACE FOR TRANSMITTING AND RECEIVING SERIAL DATA BETWEEN MEDICAL INSTRUMENTS

[75] Inventors: Curt C. Johansen, Everett; Mark P. Moore, Kent; Edward H. Hann, Woodinville, all of Wash.

[73] Assignee: Physio-Control Corporation, Redmond, Wash.

[21] Appl. No.: 334,623

[22] Filed: Nov. 4, 1994

[51] Int. Cl.⁶ ......................................................... A61N 1/08
[52] U.S. Cl. ................................................... 607/60; 607/5
[58] Field of Search ................................. 607/2, 5–8, 60

[56] References Cited

U.S. PATENT DOCUMENTS

| | | | |
|---|---|---|---|
| 4,053,951 | 10/1977 | Hudspeth et al. | 128/671 |
| 4,096,856 | 6/1978 | Smith et al. | 128/4.19 D |
| 4,097,113 | 6/1978 | McKelvy | 339/256 R |
| 4,628,935 | 12/1986 | Jones et al. | 607/5 |

*Primary Examiner*—William E. Kamm
*Attorney, Agent, or Firm*—Christensen, O'Connor, Johnson & Kindness PLLC

[57] ABSTRACT

A communication interface for transmitting serial data between a first and a second interconnectable medical instrument. A set of vertically aligned, horizontally extending leaf springs are disposed on opposing surfaces of the first and second medical instruments. A pair of serial data transfer circuits within the first and second medical instruments transmit and receive serial data through a pair of the leaf springs.

6 Claims, 5 Drawing Sheets

५,५४९,६५९

COMMUNICATION INTERFACE FOR TRANSMITTING AND RECEIVING SERIAL DATA BETWEEN MEDICAL INSTRUMENTS

FIELD OF THE INVENTION

The present invention relates to connectors and associated communication circuits for transmitting data between interconnectable medical instruments.

BACKGROUND OF THE INVENTION

The LIFEPAK 5® monitor and defibrillator produced by Physio-Control Corporation of Redmond, Wash., is a multicomponent medical instrument having an EKG monitor and a defibrillator. The monitor records and analyzes a patient's EKG signal while the defibrillator produces a high energy defibrillation pulse to terminate ventricular or atrial fibrillation. The LIFEPAK 5® monitor and defibrillator can be secured together as a single unit, having both monitoring and defibrillation capability. Alternatively, each component may be used separately when only one function is desired. Details of the interconnection are described in U.S. Pat. Nos. 4,096,856 and 4,097,113, which are expressly incorporated by reference herein.

When the two components of the LIFEPAK 5® are interconnected, five electrical contacts in the form of vertically spaced and horizontally extending leaf springs on the monitor are engaged by five corresponding contacts on the defibrillator. The top two contacts are used to transmit EKG data received from the defibrillator's hard paddles to the monitor. The center contacts are connected to isolated ground. The bottom two contacts are dedicated to operation of the instrument in a "synchronized cardioversion mode" in which the EKG monitor analyzes the EKG data from the top contacts or other EKG input and transmits a "sync pulse" to the defibrillator by way of the bottom contact when an R wave in a QRS complex is detected. The defibrillator signals the monitor that synchronized cardioversion mode is selected by applying a D.C. voltage signal to the contact immediately above the bottom sync pulse contact. Upon receipt of a sync pulse, the defibrillator delivers a defibrillation pulse to the patient.

While the LIFEPAK 5® constituted an advance in the field of separable medical components that could be used separately or interconnected to function cooperatively, the interchange between the units was quite limited.

SUMMARY OF THE INVENTION

The present invention provides an improved communication interface that transmits coded serial data between two connectable medical instruments. The interface is comprised of two corresponding sets of contacts located on opposing surfaces of the medical instruments. When the medical instruments are coupled together, the sets of contacts of the communication interface are engaged. Each set of contacts includes a plurality of vertically aligned, horizontally extending leaf spring contacts. A serial data transfer circuit in each medical instrument includes a transmit output coupled to one of the leaf springs and a receive input coupled to another of the leaf springs. When the medical instruments are connected, the transmit outputs of the serial data transfer circuit are coupled to the receive inputs of a corresponding serial data transfer circuit.

Additionally, one communication interface includes an input-output port having an input pin coupled to the receive input on the serial data transfer circuit and an output pin coupled to the same leaf spring as the transmit output of the serial data transfer circuit. A microprocessor reads the input pin of the input-output port to determine if the connected medical instrument is requesting that signals be sent in a nonserial format. If so, the communication interface transmits signals to the connected medical instrument by toggling the output pin on the input-output port.

The result is a set of interconnectable components that can be used independently, or which can be joined to function cooperatively by the interchange of coded serial data. In the preferred embodiment, the monitor can still be used with less sophisticated defibrillators which do not have serial data transfer capacity.

DETAILED DESCRIPTION OF THE PREFERRED EMBODIMENT

Figure 1:
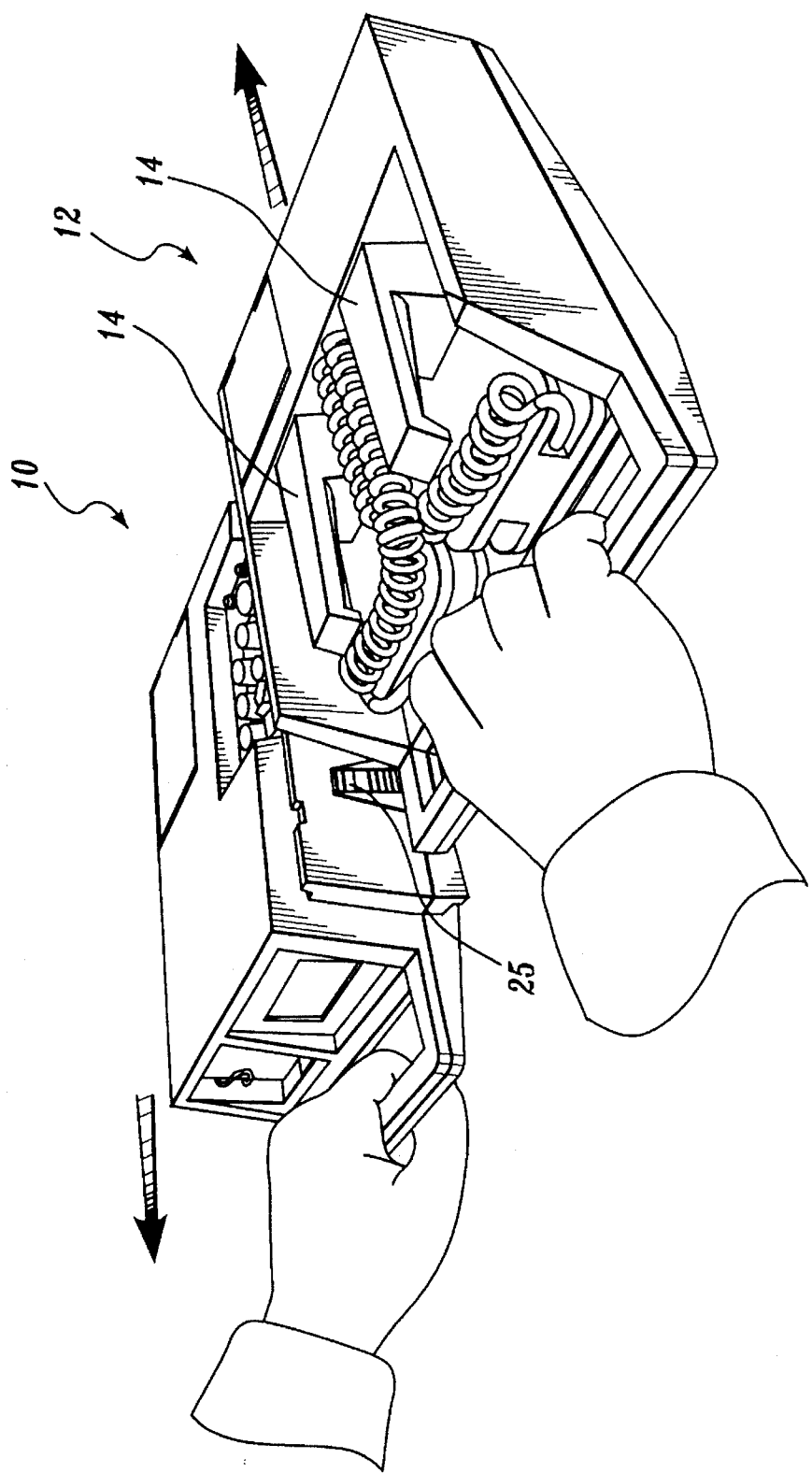
FIG. 1 is a perspective of an interconnectable EKG monitor and defibrillator having a communication interface for transmitting and receiving serial data between medical instruments in accordance with the present invention.
Figure 2:
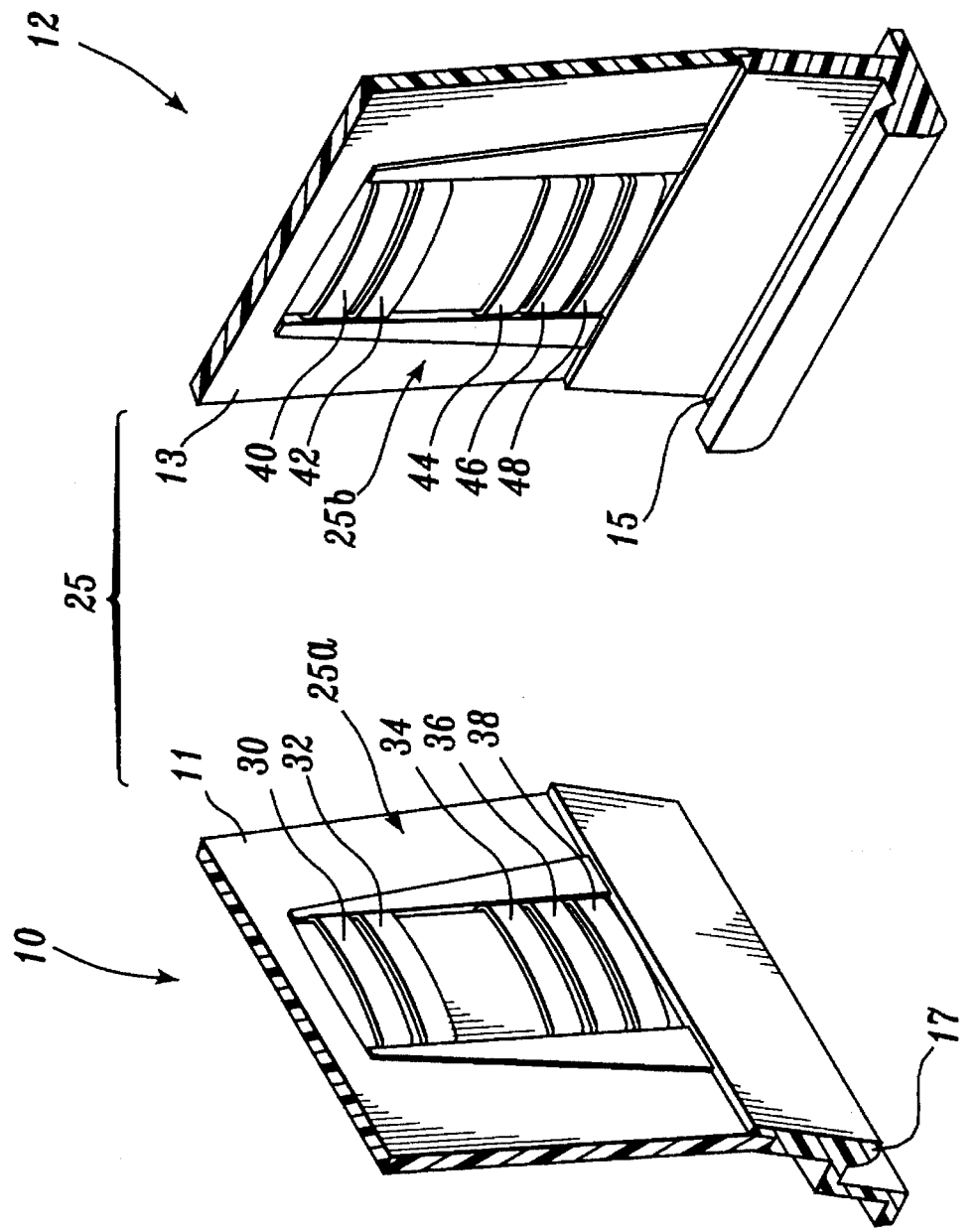
FIG. 2 is a fragmentary perspective view of the mating communication interface of FIG. 1.

FIG. 1 shows a multicomponent medical instrument having a communication interface for transmitting and receiving serial data between medical instruments in accordance with the present invention. The medical instrument includes an electrocardiogram (EKG) monitor 10 and a defibrillator 12. The EKG monitor 10 and defibrillator 12 are secured together by a cooperating tongue and groove found on opposing surfaces of the respective components. As best seen in FIG. 2, the defibrillator 12 has a side face 13 that abuts a side face 11 on the EKG monitor 10 when the defibrillator is secured to the EKG monitor. Along the base of the side face 13 is a groove 15 that cooperates with a tongue 17 disposed on the bottom surface of the EKG monitor 10. Additional details of the tongue and groove connection are set forth in U.S. Pat. No. 4,096,845.

To transmit serial data between the EKG monitor and the defibrillator, an electrical connector 25 is provided. The electrical connector is comprised of two sets of vertically aligned, horizontally extending leaf springs. A first set of leaf springs 25a, found on the EKG monitor includes five horizontally extending leaf springs 30, 32, 34, 36 and 38. Opposing the leaf springs on the EKG monitor is a second set of leaf springs 25b that includes five vertically aligned, horizontally extending leaf springs 40, 42, 44, 46 and 48. When the tongue 17 on the EKG monitor is fitted within the groove 15 on the defibrillator, leaf spring 30 engages leaf spring 40, leaf spring 32 engages leaf spring 42, leaf spring 34 engages leaf spring 44, leaf spring 36 engages leaf spring 46, and leaf spring 38 engages leaf spring 48. Although the leaf springs 40, 42, 44, 46 and 48 are described as being disposed on a defibrillator, those skilled in the art will recognize that the leaf springs could be disposed on other types of medical instruments such as cardiac pacers, etc.

In operation, the EKG monitor 10 senses the patient's electrocardiogram signal through a set of EKG electrodes (not shown). The EKG monitor displays the patient's electrocardiogram signal on a display screen for a physician or medical technician to observe. If desired, the electrocardiogram signal can be printed on a strip chart.

The defibrillator 12 includes a pair of paddles 14 (see on FIG. 1) used to apply a defibrillation pulse to the patient if necessary. When the defibrillator and monitor are coupled together, the defibrillation paddles 14 can be used to sense a patient's electrocardiogram signal if no special purpose EKG leads are available. The electrocardiogram signal sensed by the defibrillation paddles is transferred from the defibrillator to the EKG monitor via the electrical connector when the defibrillator 12 is coupled to the EKG monitor 10.

The prior art LIFEPAK 5® monitor and defibrillator uses essentially the same arrangement of leaf spring contacts as the communication interface of the present invention, but the contacts are dedicated to different operations. In the LIFEPAK 5®, the leaf springs 34 and 44 are grounded to provide a reference potential. Electrocardiogram signals received from hard paddles on the defibrillator are transmitted from leaf spring 40 on the defibrillator to leaf spring 30 on the EKG monitor and from leaf spring 42 on the defibrillator to leaf spring 32 on the EKG monitor. The defibrillator 12 can be set to provide a synchronized defibrillation pulse that is delivered at a predefined time after an R wave in the patient's EKG signal is detected. When the defibrillator is so configured, a D.C. logic signal "sync on" is applied to leaf spring 46 and is received by the EKG monitor on leaf spring 36. The EKG monitor determines whether the defibrillator is in synchronized cardioversion mode by reading the voltage on leaf spring 36. If the defibrillator is operating in the synchronized cardioversion mode, the EKG monitor analyzes the EKG signals received on leaf springs 30 and 32 in order to detect the occurrence of an R wave. Once an R wave has been detected, the EKG monitor applies the "sync pulse" on leaf spring 38, which is received on leaf spring 48, thereby causing the defibrillation pulse to be applied to the patient at the correct time.

The EKG monitor in accordance with the present invention has the ability to transmit and receive coded serial data with a cooperating medical instrument. This coded serial data may include indications of the status of an instrument, operating instructions entered by a user, physiological signals received by the instrument, etc. However, the communication circuit formerly used to drive the electrical connector 25 shown in FIG. 3 does not allow for the transfer and receipt of serial data. Therefore, the present invention is an improvement of the communication circuit to allow serial data to be transmitted between medical instruments equipped with similar connectors. In addition to transmitting and receiving serial data, preferably a communication circuit coupled to the connector detects whether an attached medical instrument is transmitting serial data or is expecting a sync pulse to be transmitted as a change in logic levels on one of the leaf springs of the connector.

Figure 3:
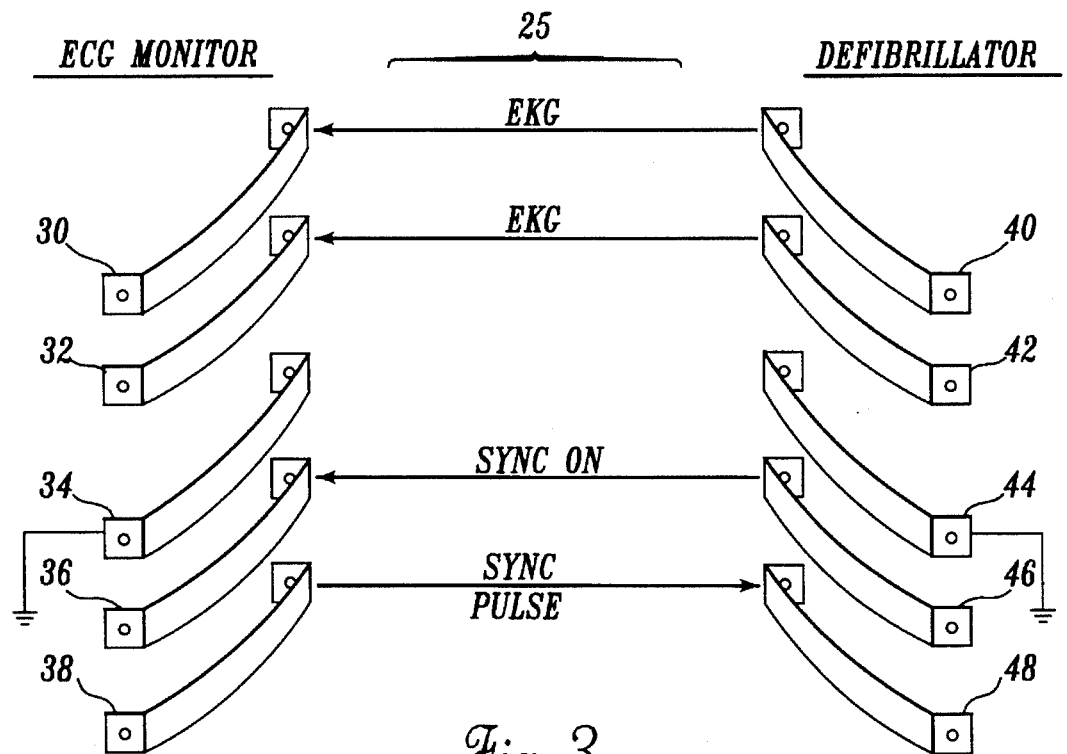
FIG. 3 is a diagrammatic perspective of a prior art electrical connector that transmits electrical signals between an EKG monitor and defibrillator.
Figure 4:
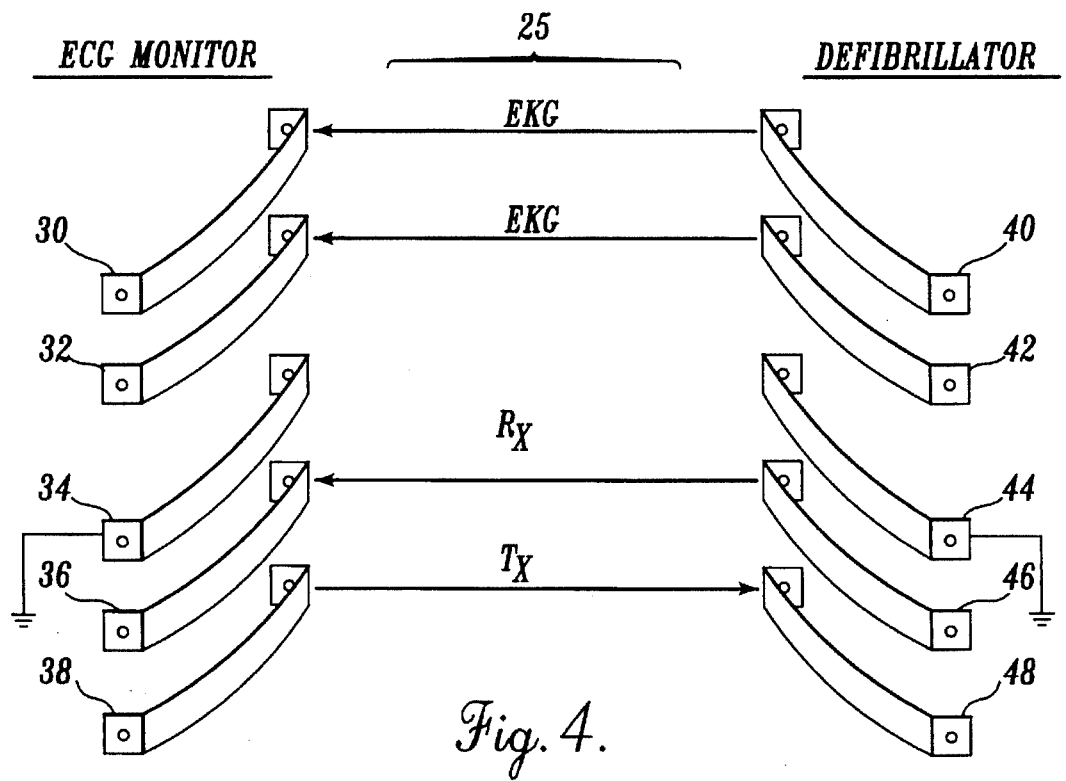
FIG. 4 is a diagrammatic perspective showing how an electrical connector of the present invention is used to transmit serial data between a pair of medical instruments.

As shown in FIG. 4, the electrical connector 25 used in the present invention is physically unchanged from the electrical connector shown in FIG. 3 and described above. The left side of the connector 25 found in the EKG monitor is driven by a communication circuit (not shown) having the ability to receive serial data on the leaf spring 36 and transmit serial data on the leaf spring 38. The right side of the connector 25 is found in a defibrillator or other medical instrument that is coupled to the EKG monitor. A communication circuit (also not shown) within the defibrillator transmits serial data from leaf spring 46 and receives serial data on leaf spring 48.

Figure 5:
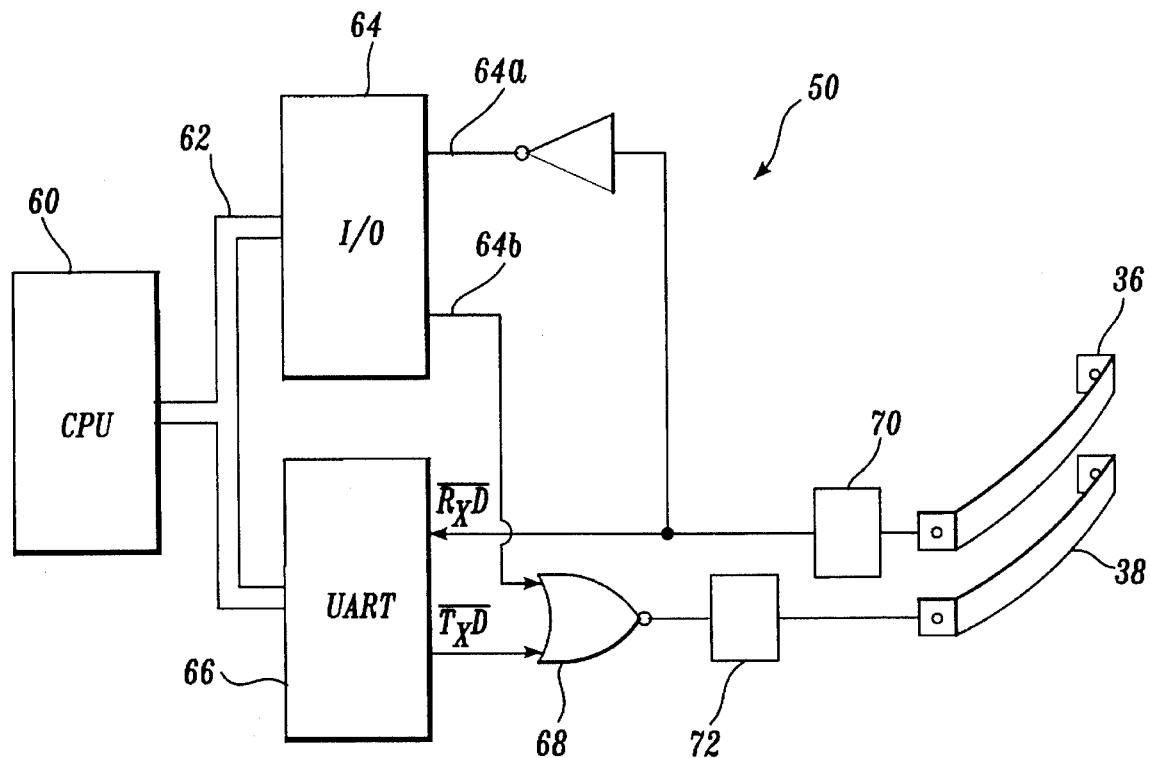
FIG. 5 is a block diagram of a communication circuit that transmits and receives serial data from a medical instrument coupled to the connector according to the present invention.

Turning now to FIG. 5, in accordance with the present invention, a communication circuit 50 found in the EKG monitor includes a central processing unit (CPU) 60, an input-output port 64, a UART 66 and a NOR gate 68. The CPU 60 is coupled to the input-output port 64 and the UART 66 via a set of data/address leads 62. A receive data pin ($\overline{RxD}$) on the UART 66 is coupled through an isolation circuit 70 to the leaf spring 36. A transmit pin ($\overline{TxD}$) pin of the UART 66 is coupled to an input of the NOR gate 68. The output of the NOR gate is coupled through an isolation circuit 72 to the leaf spring 38. Another input of the NOR gate 68 is coupled to an output pin 64b of the input-output port 64. An input pin 64a of the input-output port 64 is coupled through an inverter 74 to the $\overline{RxD}$ pin on the UART 66. The isolation circuits 70 and 72 preferably comprise known optoisolation circuits.

The communication circuit 50 operates to transmit and receive both serial data from medical instruments having this capability, and to receive EKG data and provide sync pulses to defibrillators that do not have serial data transfer capability. To determine whether a connected defibrillator is requesting a sync pulse to be provided upon the detection of an R wave, the CPU 60 reads the input pin 64a of the input-output port 64. If a logic high signal is detected for more than a predetermined duration, the EKG monitor assumes the defibrillator is operating in the synchronized cardioversion mode. When an R wave is detected in the patient's EKG wave form, the CPU transmits a sync pulse by strobing the output pin 64b on the input-output port 64. To send serial data to a defibrillator having serial communication capability, the CPU transfers parallel data over the set of data/address leads 62 to the UART 66. The UART serializes and transmits the data.

Figure 6:
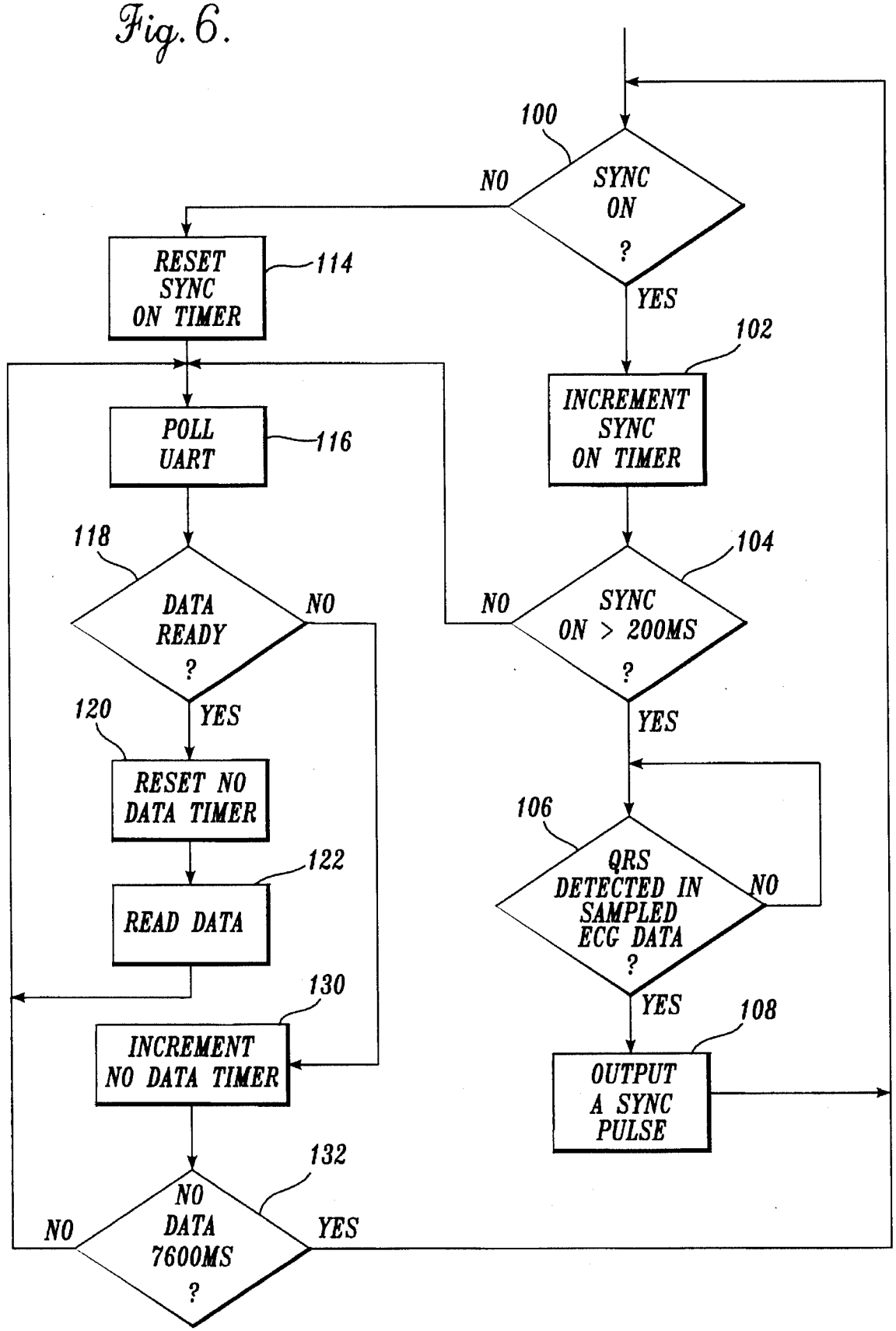
FIG. 6 is a flow chart showing the steps performed by the communication circuit shown in FIG. 5 to determine whether a connected medical instrument is transmitting serial data.

FIG. 6 is a flow chart showing the steps performed by the CPU 60 within the communication circuit 50 to determine whether a connected medical instrument is transmitting serial data or is requesting a sync pulse to be provided on leaf spring 38. Beginning with a step 100, the CPU samples the voltage on input pin 64a (shown in FIG. 5) to determine whether a "sync on" signal is present on leaf spring 36. If the sync on signal is present, an internal timer within the CPU is incremented at a step 102. At a step 104, the CPU determines whether the sync on signal has been present for more than a predefined period, such as 200 milliseconds. If not, the CPU jumps to step 116 to determine whether the serial data has been received by the UART as will be described below.

Once the sync on signal has been present for more than 200 milliseconds, the CPU proceeds from step 104 to a step 106 that analyzes the patient's EKG signal. The EKG data is analyzed for the presence of an R wave within a QRS complex according to techniques well known to those skilled in the art of medical electronics. If no R wave is detected, the CPU continues to analyze the EKG data until an R wave is detected. Upon the detection of an R wave, the CPU outputs a sync pulse by toggling the voltage on the output pin 64b of the input-output port 64 (shown in FIG. 5) at a step 108. The sync pulse informs the defibrillator that it should apply a defibrillation pulse to the patient. After the sync pulse has been provided, the CPU loops back to step 100 and determines whether the "sync on") signal is still present.

If no "sync on" signal is detected at step 100, the CPU resets the sync on timer at a step 114. The CPU then polls the UART at a step 116 and determines whether serial data has been received. If data has been received, the CPU then determines whether the received data is ready to be read by the CPU at a step 118. If data is ready to be read, the CPU resets a "no data" timer at a step 120 and reads the received data from the UART at a step 122. After the data has been read, the CPU loops back to step 116 and polls the UART to determine if more data has been received. If, after polling the UART, the CPU determines that no serial has been received or data has been received but is not yet ready to be read, the CPU increments the "no data" timer that tracks the time since data has been received at a step 130. At a step 132, the CPU determines whether more than a predefined period, such as 600 milliseconds, has passed since serial data was received by the UART. If time between the last serial data transmission is less than the predefined period, the CPU loops back to step 116 and polls the UART to see if a new serial data transmission has been received. If more than the predefined period has passed since the last serial data transmission, the CPU loops back to step 100 and again determines whether the "sync on" signal is present on leaf spring 36. Initially, the "no data" timer is set to a value more than the predetermined time (i.e., 660 milliseconds) so that if no data is received by the UART on the first pass, the answer to step 132 will be yes.

As can be seen from the above description, the communication circuit within the EKG monitor monitors whether a medical instrument connected to it is transmitting serial data or is operating in a synchronized cardioversion mode and is requesting a sync pulse to be transmitted upon detection of an R wave. For defibrillators that do transmit serial data and are operating in the synchronized cardioversion mode, the sync code signal is encoded as a serial data packet that is transmitted from the EKG monitor to the defibrillator.

Figure 7:
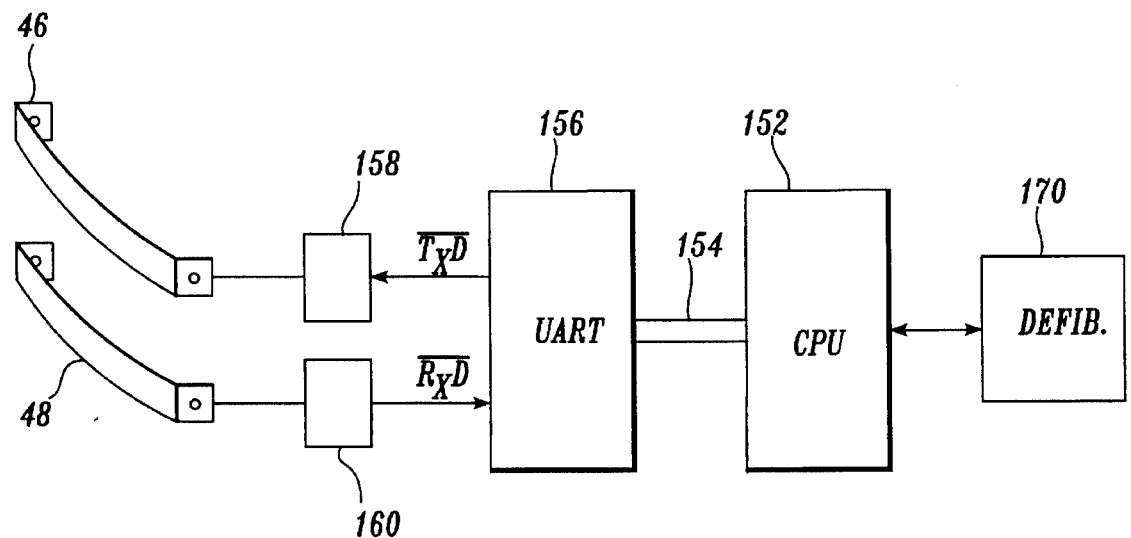
FIG. 7 (on the drawing sheet with FIG. 5) is a block diagram of a communication circuit used to transmit serial data to, and receive serial data from, the communication circuit shown in FIG. 5.

FIG. 7 is a block diagram of a communications circuit 150 found within a medical instrument that couples to and communicates with the communication circuit 50 shown in FIG. 5. The communication circuit 150 includes a CPU 152 coupled to a UART 156 via a set of address/data leads 154. The CPU 152 is preferably a model No. MC68HC11 produced by Motorola, and the UART 156 is preferably a model No. 68HC11 internal UART produced by Motorola. However, UART 156 is shown as a separate component in FIG. 7 for ease of illustration. Those skilled in the art will appreciate that other CPUs and UARTs could also be used.

A receive data pin ($\overline{RxD}$) on the UART is coupled to the leaf spring 48 through an isolation circuit 160. A transmit output pin ($\overline{TxD}$) on the UART is coupled to the leaf spring 46 through the isolation circuit 158. The CPU 152 controls the operation of a medical instrument such as a defibrillator 170 in a manner well known to those of ordinary skill in the art. Data to be transmitted from the medical instrument to the connected EKG monitor is transferred from the CPU 152 to the UART 156. The UART serializes and transmits the data. Serial data received by the communication circuit is converted by the UART to parallel form to be read by the CPU 152.

As can be seen from the above description, the communication interface of the present invention allows sophisticated data transmissions to take place between interconnected medical instruments and is compatible with prior art interfaces that do not have serial transfer capability without the addition of additional contacts.

While the preferred embodiment of the invention has been illustrated and described, it will be appreciated that various changes can be made therein without departing from the spirit and scope of the invention. It is therefore intended that the scope of the invention be determined solely from the following claims.

The embodiments of the invention in which an exclusive property or privilege is claimed are defined as follows:

1. A communication interface for transmitting data between a first and a second interconnectable medical instrument, comprising:

a first set of horizontally extending leaf spring contacts for mounting on the first medical instrument;

a second set of horizontally extending leaf spring contacts for mounting on the second medical instrument, and positioned to engage the contacts of the first set when the first and second medical instruments are interconnected;

a first serial communication circuit to be placed within the first medical instrument that transmits and receives serial data, the communication circuit having a transmit output coupled to a first leaf spring contact of said first set of leaf spring contacts and a receive input coupled to a second leaf spring contact of said first set of leaf spring contacts; and a second serial communication circuit to be placed within the second medical instrument that transmits and receives serial data, the second serial communication circuit having a transmit output coupled to a first leaf spring contact of said second set of leaf spring contacts and a receive input coupled to a second leaf spring contact of said second set of leaf spring contacts, wherein the transmit output of the first serial communication circuit is coupled to the receive input of the second serial communication circuit and the transmit output of the second serial communication circuit is coupled to the receive input of the first serial communication circuit when the first and second medical instruments are interconnected.

2. The communication interface of claim 1, wherein the first serial communication circuit further includes:

an input-output port having an input pin coupled to the receive input of the first serial communication circuit and an output pin coupled to the same leaf spring contact as the transmit output of the first serial communication circuit spring contacts.

3. The communication interface of claim 1, wherein said first and second sets of leaf spring contacts comprise five vertically aligned leaf spring contacts, wherein said transmit output of the first serial communication circuit is coupled to a bottom leaf spring contact of said first set of leaf spring contacts, said receive input of the first serial communication circuit is coupled to a leaf spring contact immediately above said bottom Leaf spring contact.

4. A communication interface for transmitting data between a first and a second interconnectable medical instrument, comprising:

a first set of vertically aligned, horizontally extending leaf springs for mounting on the first medical instrument, the first set of leaf springs arranged top to bottom including a first leaf spring, a second leaf spring disposed below the first leaf spring, a third leaf spring disposed below the second leaf spring, a fourth leaf spring disposed below the third leaf spring, and a fifth leaf spring disposed below the fourth leaf spring;

a second set of vertically aligned, horizontally extending leaf springs for mounting on the second medical instrument, the second set of leaf springs arranged top to bottom including a sixth leaf spring, a seventh leaf spring disposed below the sixth leaf spring, an eighth leaf spring disposed below the seventh leaf spring, a ninth leaf spring disposed below the eighth leaf spring, and a tenth leaf spring disposed below the ninth leaf spring, wherein said sixth leaf spring engages said first leaf spring, said seventh leaf spring engages said second leaf spring, said eighth leaf spring engages said third leaf spring, said ninth leaf spring engages said fourth leaf spring and said tenth leaf spring engages said fifth leaf spring when said first and second medical instruments are interconnected wherein said first and second leaf springs are adapted to receive ECG data from said sixth and seventh leaf springs when the first and second medical instruments are interconnected and wherein said third and eighth leaf springs are grounded;

a first serial communication circuit, for disposal in the first medical instrument, having a receive input coupled to the fourth leaf spring and a transmit output coupled to the fifth leaf spring; and a second serial communication circuit, for disposal in the second medical instrument, having a transmit output coupled to the ninth leaf spring and a receive input coupled to the tenth leaf spring.

5. A communication interface for transmitting data between a first and a second interconnectable medical instrument, comprising:

a first set of vertically aligned, horizontally extending leaf springs for mounting on the first medical instrument, the first set of five leaf springs arranged top to bottom including a first leaf spring, a second leaf spring disposed below the first leaf spring, a third leaf spring disposed below the second leaf spring, a fourth leaf spring disposed below the third leaf spring, and a fifth leaf spring disposed below the fourth leaf spring;

a second set of vertically aligned, horizontally extending leaf springs for mounting on the second medical instrument, the second set including five leaf springs arranged top to bottom including a sixth leaf spring, a seventh leaf spring disposed below the sixth leaf spring, an eighth leaf spring disposed below the seventh leaf spring, a ninth leaf spring disposed below the eighth leaf spring, and a tenth leaf spring disposed below the ninth leaf spring, wherein said sixth leaf spring engages said first leaf spring, said seventh leaf spring engages said second leaf spring, said eighth leaf spring engages said third leaf spring, said ninth leaf spring engages said fourth leaf spring and said tenth leaf spring engages said fifth leaf spring when said first and second medical instruments are interconnected wherein said first and second leaf springs are adapted to receive ECG data from said sixth and seventh leaf springs when the first and second medical instruments are interconnected and wherein said third and eighth leaf springs are grounded;

a first serial communication circuit, for disposal in the first medical instrument, having a receive input coupled to the fourth leaf spring and a transmit output coupled to the fifth leaf spring, said first serial communication circuit further including an input-output port having an input pin coupled to said fourth leaf spring and an output pin coupled to said fifth leaf spring; and a second serial communication circuit, for disposal in the second medical instrument, having a transmit output coupled to the ninth leaf spring and a receive input coupled to the tenth leaf spring.

6. In a pair of interconnectable medical instruments adapted for the transmission of data therebetween, a communication interface comprising:

a first set of horizontally extending leaf spring contacts for mounting on a first one of the pair of medical instruments;

a second set of horizontally extending leaf spring contacts for mounting on a second one of the pair of medical instruments, and positioned to engage the contacts of the first set when the first and second medical instruments are interconnected;

first serial communication circuit means for disposal within the first medical instrument for transmitting and receiving serial data, the communication circuit means having a transmit output coupled to a first leaf spring contact of said first set of leaf spring contacts and a receive input coupled to a second leaf spring contact of said first set of left spring contacts; and second serial communication circuit means for disposal within the second medical instrument for transmitting and receiving serial data, the second serial communication circuit means having a transmit output coupled to a first left spring contact of said second set of leaf spring contacts and a receive input coupled to a second leaf spring contact of said second set of left spring contacts, wherein the transmit output of the first serial communication circuit means is coupled to the receive input of the second serial communication circuit means and the transmit output of the second serial communication circuit means is coupled to the receive input of the first serial communication circuit means when the first and second medical instruments are interconnected.

* * * * *